(12) United States Patent
Musser

(10) Patent No.: US 8,268,882 B2
(45) Date of Patent: Sep. 18, 2012

(54) TRIPTOLIDE C-RING DERIVATIVES AS ANTICANCER AGENTS AND IMMUNE MODULATORS

(75) Inventor: John H. Musser, San Carlos, CA (US)

(73) Assignee: Pharmagenesis, Inc., Redwood City, CA (US)

( * ) Notice: Subject to any disclaimer, the term of this patent is extended or adjusted under 35 U.S.C. 154(b) by 0 days.

(21) Appl. No.: 13/147,587

(22) PCT Filed: Feb. 4, 2010

(86) PCT No.: PCT/US2010/023220
§ 371 (c)(1),
(2), (4) Date: Aug. 2, 2011

(87) PCT Pub. No.: WO2010/091193
PCT Pub. Date: Aug. 12, 2010

(65) Prior Publication Data
US 2011/0288166 A1    Nov. 24, 2011

Related U.S. Application Data

(60) Provisional application No. 61/150,207, filed on Feb. 5, 2009.

(51) Int. Cl.
*A61K 31/365* (2006.01)
*C07D 493/14* (2006.01)
*C07D 493/22* (2006.01)
(52) U.S. Cl. ......... 514/463; 514/468; 549/229; 549/297
(58) Field of Classification Search .................. 514/463, 514/468; 549/229, 297; 435/375
See application file for complete search history.

(56) References Cited

U.S. PATENT DOCUMENTS

| 4,005,108 | A |   | 1/1977  | Kupchan       |         |
|-----------|---|---|---------|---------------|---------|
| 5,294,443 | A |   | 3/1994  | Lipsky et al. |         |
| 6,004,999 | A | * | 12/1999 | Jung et al.   | 514/468 |
| 6,150,539 | A |   | 11/2000 | Musser        |         |
| 6,620,843 | B2|   | 9/2003  | Fidler et al. |         |

FOREIGN PATENT DOCUMENTS

| WO | WO 02/17931   | A1 | 3/2002  |
| WO | WO 03/101951  | A2 | 12/2003 |
| WO | WO 2004/058246| A1 | 7/2004  |
| WO | WO 2004/075853| A2 | 9/2004  |
| WO | WO 2005/020887| A2 | 3/2005  |
| WO | WO 2005/084365| A2 | 9/2005  |

OTHER PUBLICATIONS

Gleichmann et al., "Graft-versus-host reactions: clues to etiopathology of a spectrum of immunological diseases", Immunol. Today, vol. 5, No. 11, pp. 324-332 (1984).
He et al., "Nueroprotective effects of Tripterygium Wilforddi Hook F monomer $T_{10}$ on glutamate induced PC12 cell line damage and its mechanism", J. of Peking University, vol. 35, No. 3, pp. 252-255 (2003) *English Abstract*.
Korngold and Sprent, "Lethal graft-versus-host disease after bone marrow transplantation across minor histocompatability barriers in mice", J. Exp. Med., vol. 148, pp. 1687-1698 (1978).
Krishna et al., "PG490-88, a derivative of triptolide , blocks bleomycin-induced lung fibrosis", Am. J. Pathology, vol. 158, No. 3, pp. 997-1004 (2001).
Kupchan et al., "Triptolide and tripdiolide, novel antiluekemic diterpenoid triepoxides from *Tripterygium wilfordii*", J. Am. Chem. Soc., vol. 94, pp. 7194-7195 (1972).
Liu et al., "Immunosuppressant triptolide inhibits dendritic cell-mediated chemoattraction of neurophils and T cells through inhibiting stat3 phosphorylation and NF-κB activation", Biochem. Biophys. Res. Commun., vol. 345, No. 3, pp. 1122-1130 (2006).
Ma et al., "16-Hydroxytriptolide: An active compound from *Trypterygium wilfordii*", J. Chin. Pharm. Sci., vol. 1, No. 2, pp. 12-18 (1992).
Murase et al., "Hamster-to-rat heart and liver xenotransplantation with FK506 plus antiproliferative drugs", Transplantation, vol. 55, pp. 701-708 (1993).
Ono and Lindsey, "Improved technique of heart transplantation in rats", J. Thor. Cardiovasc. Surg., vol. 57, No. 2, pp. 225-229 (1969).
Phillips et al., "Triptolide induces pancreatic cancer cell death via inhibition of heat shock protein 70", Cancer Res., vol. 67, No. 19, pp. 9407-9416 (2007).
Pu et al., "Effects of triptolide on T lymphocyte functions in mice", Acta Pharmacologica Sinica, vol. 11, No. 1, pp. 76 (1990) *English Abstract*.
Wang and Morris, "Effect of splenectomy and mono- or combination therapy with rapamycin, the morpholinoethyl ester of mycophenolic acid and deoxyspergulin on cardiac xenograft survival", Transplantation Proc., vol. 23, pp. 699-702 (1991).
Zhou et al., "Several monomes from *Tripterygium wilfordii* inhibit proliferation of glioma cells in vitro", Chin. J. Cancer, Vo. 21, No. 10, pp. 1106-1108 (2002) *English Abstract*.

\* cited by examiner

*Primary Examiner* — Kristin Bianchi
(74) *Attorney, Agent, or Firm* — King & Spalding LLP; Peter J. Dehlinger; Susan J. Myers Fitch

(57) ABSTRACT

Disclosed are compounds based on C- and D-ring modifications of triptolide and hydroxylated triptolide, for use in therapy, such as antiproliferative, anticancer, and immunosuppressive therapy.

14 Claims, 8 Drawing Sheets

PG762

PG830

PG757

PG782

TRIPTOLIDE C-RING DERIVATIVES AS ANTICANCER AGENTS AND IMMUNE MODULATORS

CROSS-REFERENCE TO RELATED APPLICATIONS

This application is a U.S. National Stage filing under 35 U.S.C. 371 of International Patent Application No. PCT/US2010/023220, filed 4 Feb. 2010, which claims benefit under 35 U.S.C. §119(e) to U.S. Provisional Patent Application Ser. No. 61/150,207, filed 5 Feb. 2009, the disclosures of which are incorporated herein by reference in their entirety.

FIELD OF THE INVENTION

The present invention relates to compounds useful as immunosuppressive, anti-inflammatory and anticancer agents.

REFERENCES

Gleichmann, E. et al., *Immunol. Today* 5:324 (1984).
He, Q. et al., *Beijing Da Xue Xue Bao* 35:252-5 (June 2003).
Korngold, R. and Sprent, *J. Exp. Med.* 148:1687 (1978).
Krishna, G. et al., *Am. J. of Pathology* 158(3):997-1004 (March 2001).
Kupchan, S. M. et al., *J. Am. Chem. Soc.* 94:7194 (1972).
Kupchan, S. M. et al., U.S. Pat. No. 4,005,108 (1977).
Lipsky et al., U.S. Pat. No. 5,294,443 (1994).
Ma et al, *J. Chin. Pharm. Sci.* 1:12 (1992).
Murase, N. et al., *Transplantation* 55:701 (1993).
Ono and Lindsey, *J. Thor. Cardiovasc. Surg.* 57(2):225-29 (1969).
Pu, L. et al., *Zhongguo Yaoll Xuebao* 11:76 (1990).
Wang, J. and Morris, R. E., *Transplantation Proc.* 23:699 (1991).
Wang, X. et al., PCT Pubn. No. WO 2002/17931 (2002).
Zhou, Y. X. et al., *Ai Zheng* 21(10):1108-8 (October 2002).

BACKGROUND OF THE INVENTION

Immunosuppressive agents are widely used in the treatment of autoimmune disease and in treating or preventing transplantation rejection, including the treatment of graft-versus-host disease (GVHD). Common immunosuppressive agents include azathioprine, corticosteroids, cyclophosphamide, methotrexate, 6-mercaptopurine, vineristine, and cyclosporin A.

In general, none of these drugs are completely effective, and most are limited by toxicity. For example, cyclosporin A, a widely used agent, is significantly toxic to the kidney, in addition, doses needed for effective treatment may increase the patient's susceptibility to infection by a variety of opportunistic invaders.

The compound triptolide, obtained from the Chinese medicinal plant *Tripterygium wibrdii* (TW), and certain derivatives and prodrugs thereof, have been identified as having immunosuppressive activity, e.g. in the treatment of autoimmune disease, and in treating or preventing transplantation rejection, including the treatment of graft-versus-host disease (GVHD). Triptolide and certain derivatives and prodrugs thereof have also been reported to show anticancer activity. Such derivatives and prodrugs of triptolide have provided benefits relative to native triptolide in areas such as pharmacokinetics or biodistribution, e.g. by virtue of differences in lipid or aqueous solubility, or via their activity as prodrugs; however, their biological activity is often significantly less than that of native triptolide.

SUMMARY OF THE INVENTION

In one aspect, the invention provides compounds which are useful for immunosuppressive, anti-inflammatory and anticancer therapy. In one embodiment, the compounds are represented by formula I:

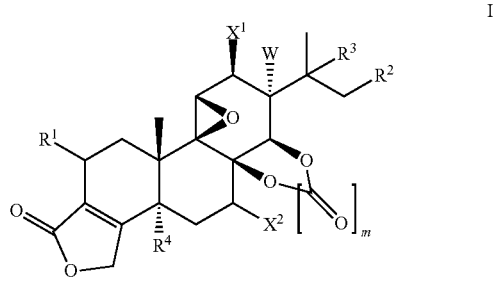

where
each of $R^1$, $R^2$, $R^3$, and $R^4$ is independently selected from hydrogen, hydroxyl, —O(CO)$_n$X, —O(CO)$_n$OR$^5$, and —O(CO)$_n$N(R$^5$)$_2$, where X is halogen, $R^5$ is hydrogen or lower alkyl, and n is 1-2,
with the proviso that at least three of $R^1$, $R^2$, $R^3$, and $R^4$ are hydrogen;
m is 1-2;
$X^2$ is halogen, such as F or Cl; and
$X^1$ is halogen, preferably Cl, and W is hydroxyl; or $X^1$ and W together form an epoxy group.
When any of each of $R^1$, $R^2$, $R^3$, and $R^4$ is selected from —O(CO)$_n$X, —O(CO)$_n$OR$^5$, or —O(CO)$_n$N(R$^5$)$_2$, the variable n is preferably 1.
In selected embodiments of formula I, each of $R^1$, $R^2$, $R^3$, and $R^4$ is hydrogen. In further selected embodiments, m=1.
in a further aspect, the invention provides compounds of structure II:

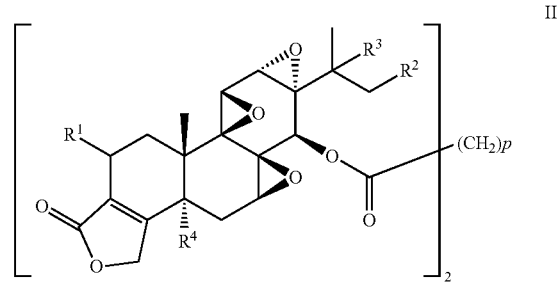

where
each of $R^1$, $R^2$, $R^3$, and $R^4$ is independently selected from hydrogen, hydroxyl, —O(CO)$_n$OR$^5$, and —O(CO)$_n$N(R$^5$)$_2$, where X is halogen, $R^5$ is hydrogen or lower alkyl, and n is 1-2, with the proviso that at least three of $R^1$, $R^2$, $R^3$, and $R^4$ are hydrogen; and p is 0-4. Preferably, when any of $R^1$, $R^2$, $R^3$, and $R^4$ is —O(CO)$_n$X, —O(CO)$_n$OR$^5$, and —O(CO)$_n$N(R$^5$)$_2$, n=1 and X is Cl. In selected embodiments, each of $R^1$, $R^2$, $R^3$, and $R^4$ is hydrogen. In further selected embodiments, p=0.

In a related aspect, the invention provides a method of effecting immunosuppression, comprising administering to a subject in need of such treatment, in a pharmaceutically acceptable vehicle, an effective amount of a compound of structure I or structure II above. The invention also provides a method of inducing apoptosis in a cell, e.g. for anticancer treatment, comprising contacting the cell with an effective amount of a compound of structure I or structure II above. Specific embodiments Of these methods may employ any of the specific embodiments of formulas I and II described above.

These and other objects and features of the invention will become more fully apparent when the following detailed description of the invention is read in conjunction with the accompanying drawings.

DETAILED DESCRIPTION OF THE INVENTION

I. Definitions

Figure 1B:
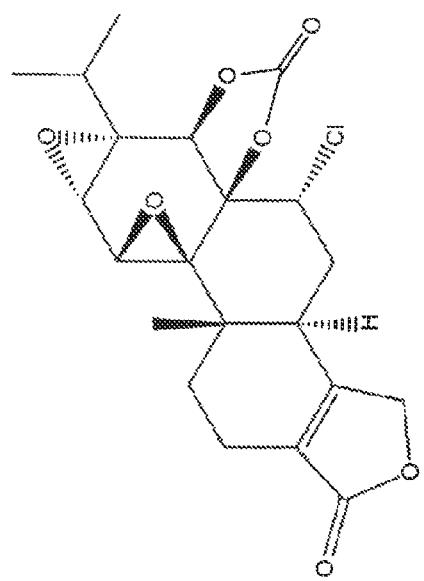
FIGS. 1A-1C show exemplary compounds of the invention which are embodiments of structure I herein.

"Alkyl" refers to a saturated acyclic monovalent radical containing carbon and hydrogen, which may be linear or branched. Examples of alkyl groups are methyl, ethyl, n-butyl, t-butyl, n-heptyl, and isopropyl. "Cycloalkyl" refers to a fully saturated cyclic monovalent radical containing carbon and hydrogen, which may be further substituted with alkyl. Examples of cycloalkyl groups are cyclopropyl, methyl cyclopropyl, cyclobutyl, cyclopentyl, ethylcyclopentyl, and cyclohexyl. "Lower alkyl" refers to such a group having one to six carbon atoms, preferably one to four carbon atoms.

"Aryl" refers to a monovalent aromatic radical having a single ring (e.g., benzene) or two condensed rings (e.g., naphthyl). As used herein, aryl is preferably monocyclic and carbocyclic (non-heterocyclic), e.g. a benzene (phenyl) ring or substituted benzene ring. By "substituted" is meant that one or more ring hydrogens is replaced with a group such as a halogen (e.g. fluorine, chlorine, or bromine), lower alkyl, nitro, amino, lower alkylamino, hydroxy, lower alkoxy, or halo(lower alkyl).

"Halogen" or "halo" refers to fluorine, chlorine, bromine, or iodine, and preferably to fluorine or chlorine.

For the purposes of the current disclosure, the following numbering scheme is used for triptolide and triptolide derivatives:

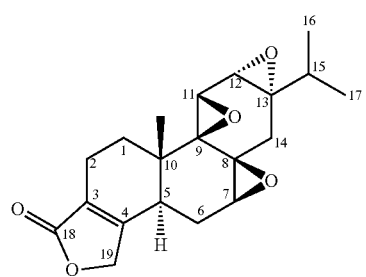

II. Invention Compounds

The compounds of the invention are derivatives of triptolide or hydroxylated triptolides, resulting from acylation of the 14-hydroxy group to generate a dimeric structure (structure II) or, preferably, in combination with ring-opening of the 7,8-epoxy group to generate a new 8,14 ring structure (structure I), as described below. The new ring structure in structure I incorporates a carbonate (—OC(O)O—) or oxalate (—OC(O)C(O)O—) moiety.

More specifically, the invention provides compounds represented by structure I:

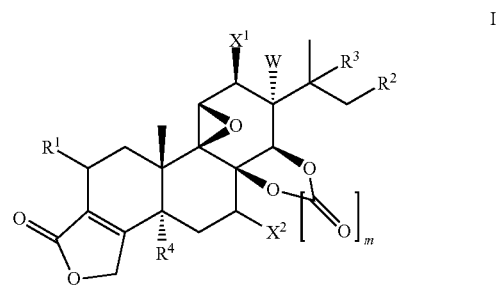

where
  each of $R^1$, $R^2$, $R^3$, and $R^4$ is independently selected from hydrogen, hydroxyl, —O(CO)$_n$X, —O(CO)$_n$OR$^5$, and —O(CO)$_n$N(R$^5$)$_2$, where X is halogen, $R^5$ is hydrogen or lower alkyl, and n is 1-2,
  with the proviso that at least three of $R^1$, $R^2$, $R^3$, and $R^4$ are hydrogen;
  m is 1-2;
  $X^2$ is halogen, such as F or Cl; and
  $X^1$ is halogen, preferably Cl, and W is hydroxyl; or $X^1$ and W together form an epoxy group.

When any of each of $R^1$, $R^2$, $R^3$, and $R^4$ is selected from —O(CO)$_n$X, —O(CO)$_n$OR$^5$, —O(CO)$_n$N(R$^5$)$_2$, the variable n is preferably 1.

In selected embodiments of formula I, each of $R^1$, $R^2$, $R^3$, and $R^4$ is hydrogen. In further selected embodiments, m=1.

In a further aspect, the invention provides dimeric compounds of structure II:

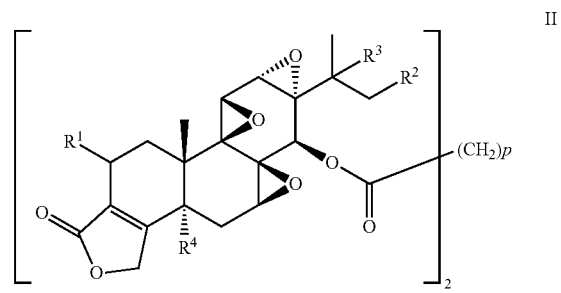

where
  each of $R^1$, $R^2$, $R^3$, and $R^4$ is independently selected from hydrogen, hydroxyl, —O(CO)$_n$X, —O(CO)$_n$OR$^5$, and —O(CO)$_n$N(R$^5$)$_2$, where X is halogen, $R^5$ is hydrogen or lower alkyl, and n is 1-2, with the proviso that at least three of $R^1$, $R^2$, $R^3$, and $R^4$ are hydrogen; and p is 0-4.

Preferably, when any of $R^1$, $R^2$, $R^3$, and $R^4$ is —O(CO)$_n$X, —O(CO)$_n$OR$^5$, and —O(CO)$_n$N(R$^5$)$_2$, n=1 and X is Cl. In selected embodiments, each of $R^1$, $R^2$, $R^3$, and $R^4$ is hydrogen.

The variable p is any of 0, 1, 2, 3, and 4; in selected embodiments, p=0, such that the polycyclic ring structures are connected via an oxalyl (—C(O)—C(O)—) linker, as in the exemplary compound designated PG782.

A. Preparation

The compounds of the invention may be prepared from triptolide or its hydroxylated derivatives. The latter include tripdiolide (2-hydroxytriptolide) and 16-hydroxytriptolide, which, along with triptolide, can be obtained from the root xylem of the Chinese medicinal plant *Tripterygium wilfordii* (TW) or from other known sources. The TW plant is found in the Fujian Province and other southern provinces of China; TW plant material can generally be obtained in China or through commercial sources in the United States. Methods for preparing triptolide, tripdiolide and 16-hydroxytriptolide are known in the art and are described, for example, in Kupchan et al. (1972, 1977); Lipsky et al. (1994); Pu et al., (1990); and Ma et al., (1992).

Compounds of structure I can be prepared from triptolide, or a triptolide derivative or analog, by reaction with a diacid chloride Cl(CO)$_m$Cl; i.e. phosgene where m=1 or oxalyl chloride where m=2. An organic base such as amine is typically included as a catalyst, although the reaction is expected to proceed without the catalyst. Depending on reaction conditions, the 12,13-epoxy compound is formed alone or together with the 12-chloro-13-hydroxy (ring-opened) analog. The compounds can be separated by standard chromatographic methods, and the latter can be converted to the former by treatment with base.

Preparations of exemplary compounds of structure I (PG757, PG762 and PG830) are described in Examples 1-2 below.

Dimeric compounds of structure II can be prepared by reacting triptolide, or a triptolide derivative or analog, with a diacid chloride Cl(CO)$_m$Cl, where m is 0 or 1, in the presence of a basic catalyst at low temperature; i.e. <0° C., preferably <−20° C. Preparation of an exemplary compound of structure 1 (PG782) is described in Example 3 below.

B. Biological Activity

The cytotoxic activity of three compounds of structure 1, designated PG757, PG762 and PG830 and one compound of structure II, designated PG782, was evaluated using a standard MIT assay, as described in Example 4. The immunosuppressive activity of these compounds was evaluated in a standard IL-2 inhibition assay, as described in Example 5.

Figure 3:
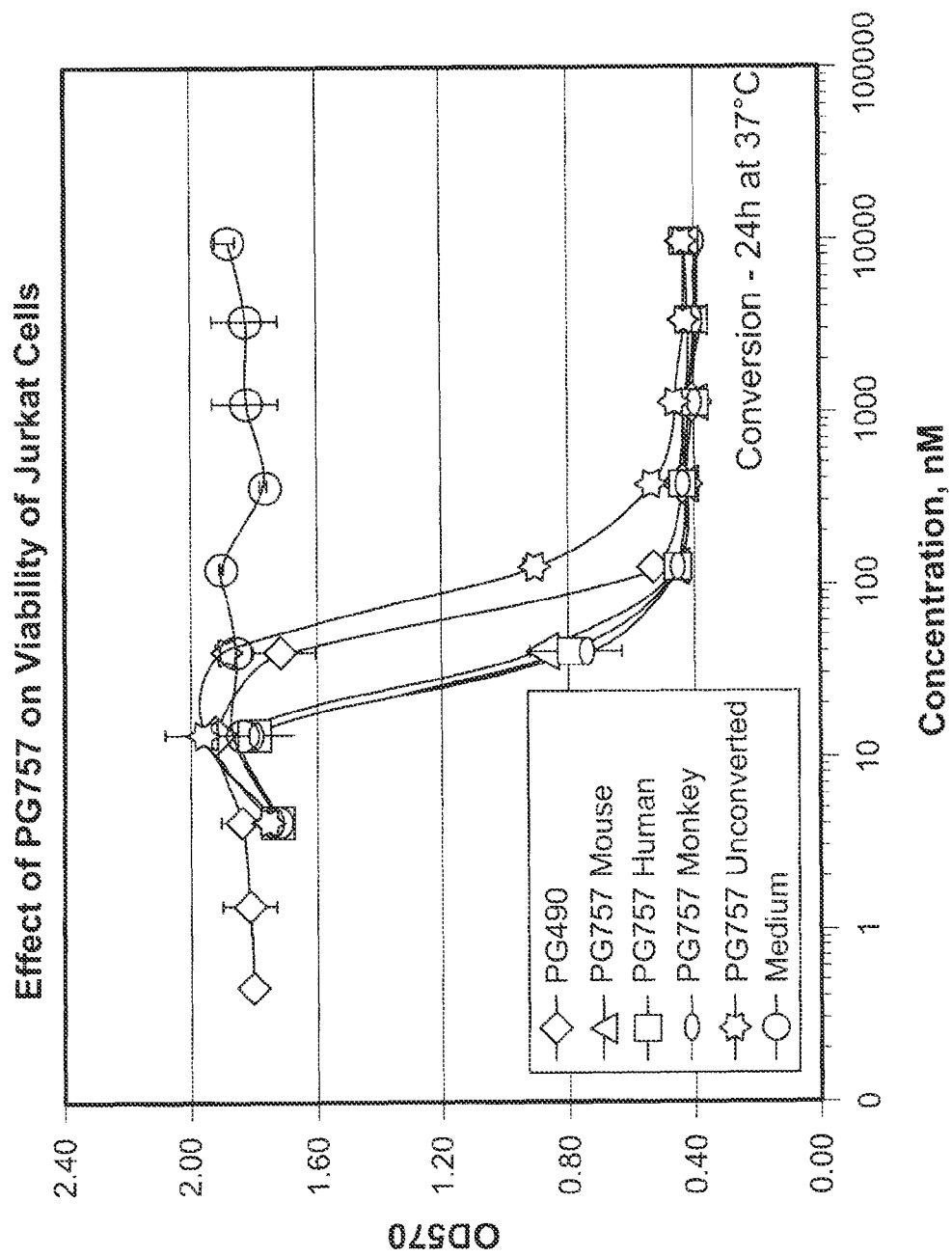
FIGS. 3-5 show the cytotoxic effect in Jurkat cells of invention compounds designated PG757, PG762, and PG782, respectively, in comparison with triptolide (designated PG490) (Example 4)
Figure 4:
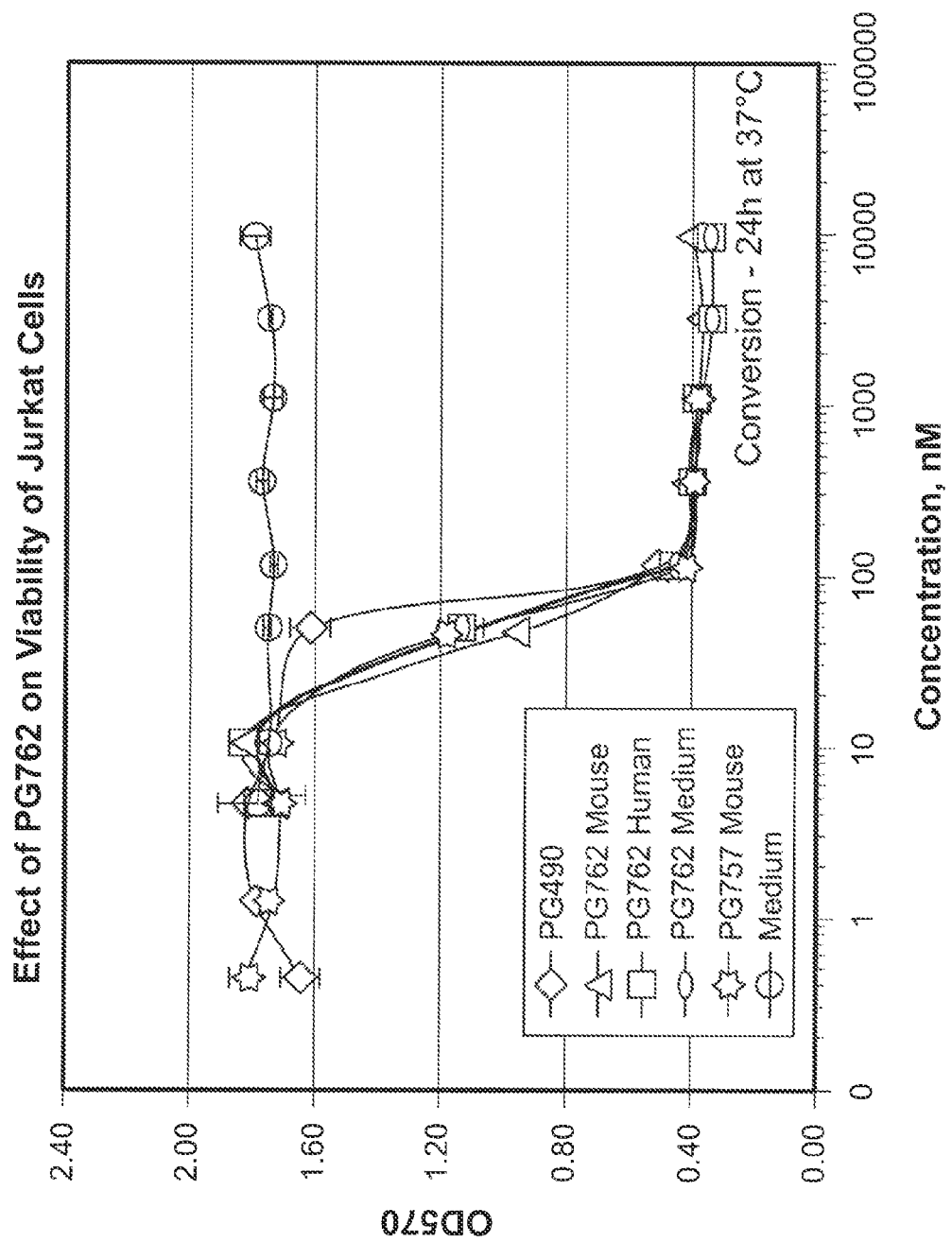
Figure 5:
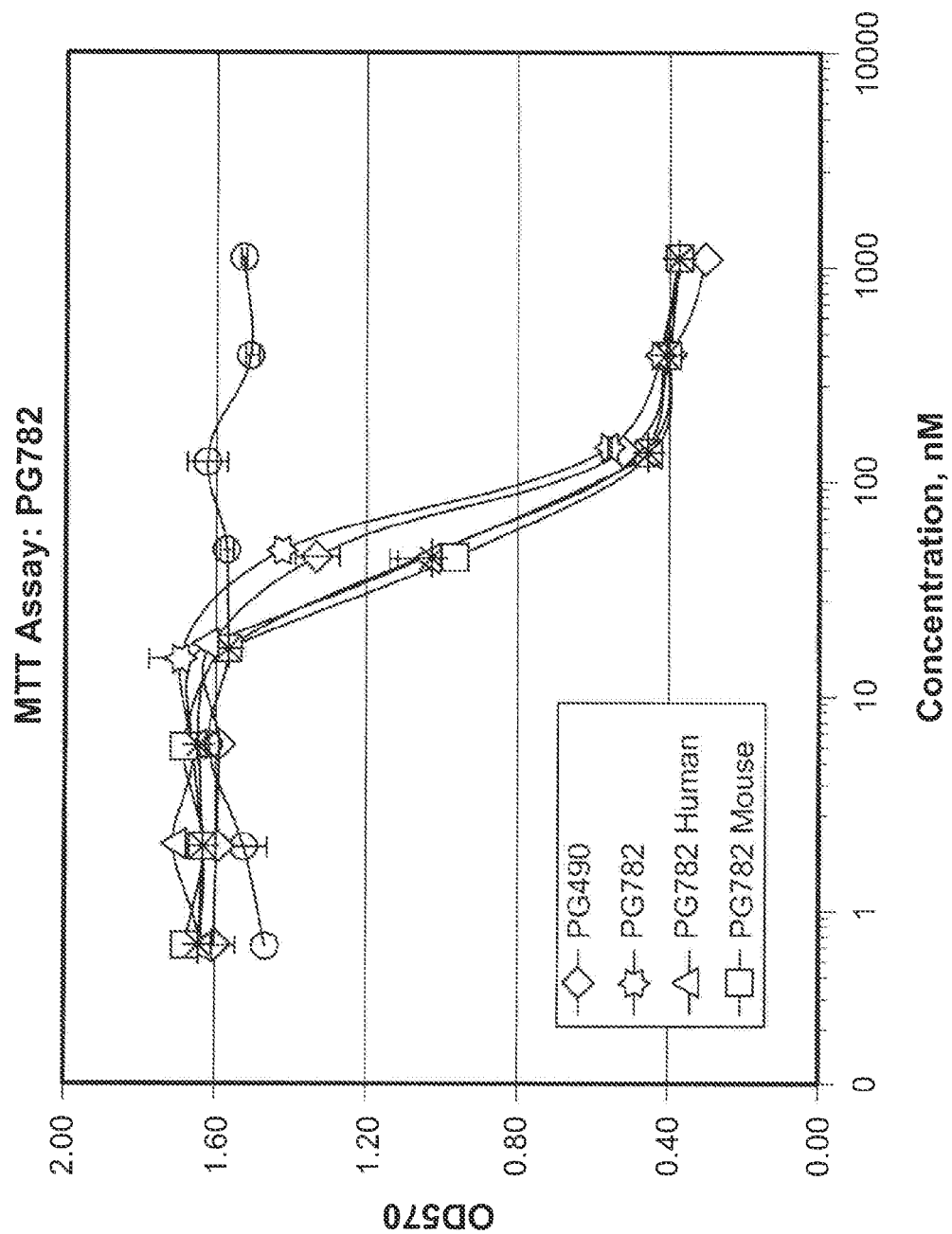
Figure 6:
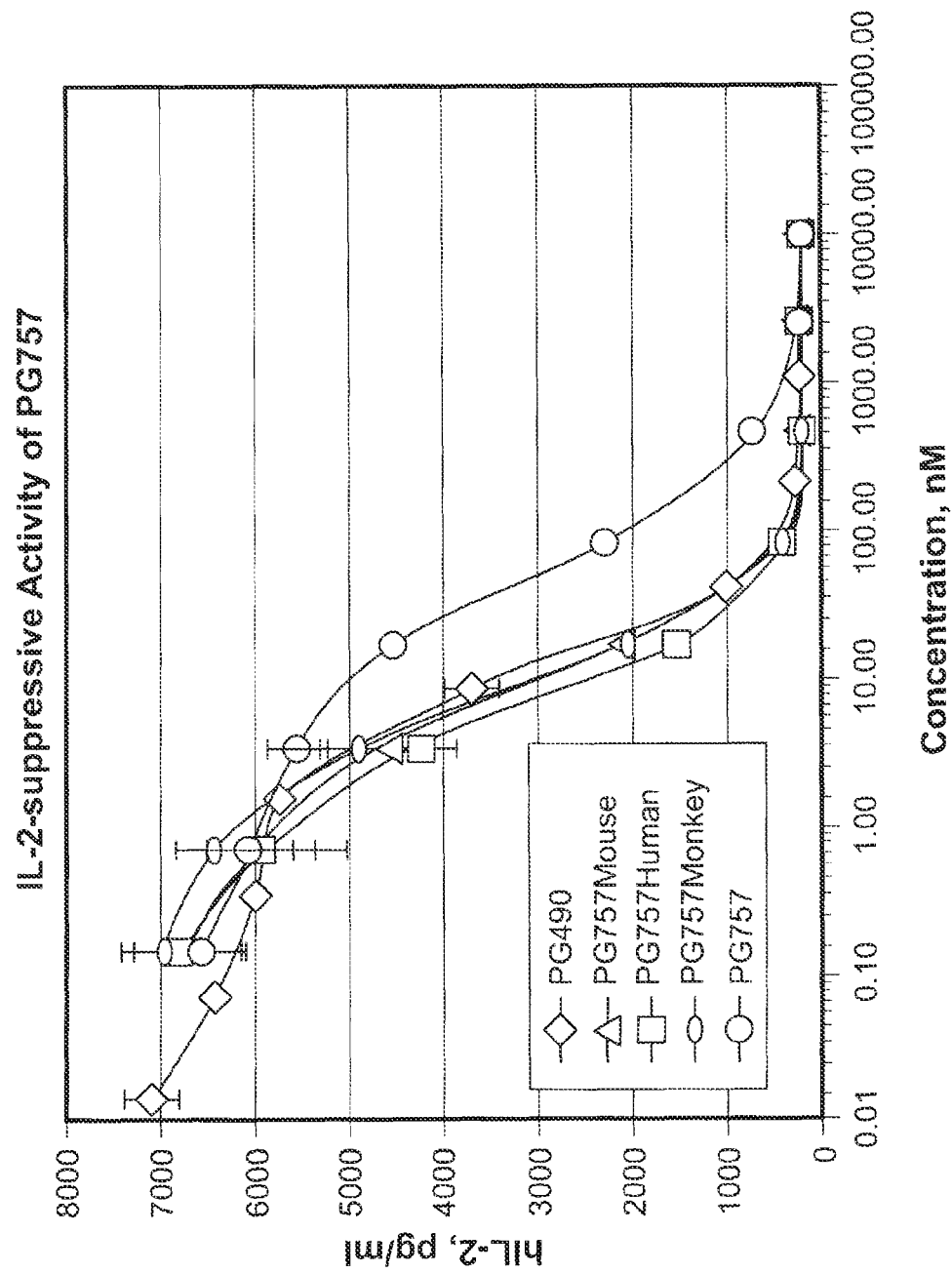
FIG. 6-8 shows inhibition of IL-2 production in Jurkat cells by invention compounds designated PG757, PG762, and PG782, respectively, in comparison with triptolide (designated PG490) (Example 5).
Figure 7:
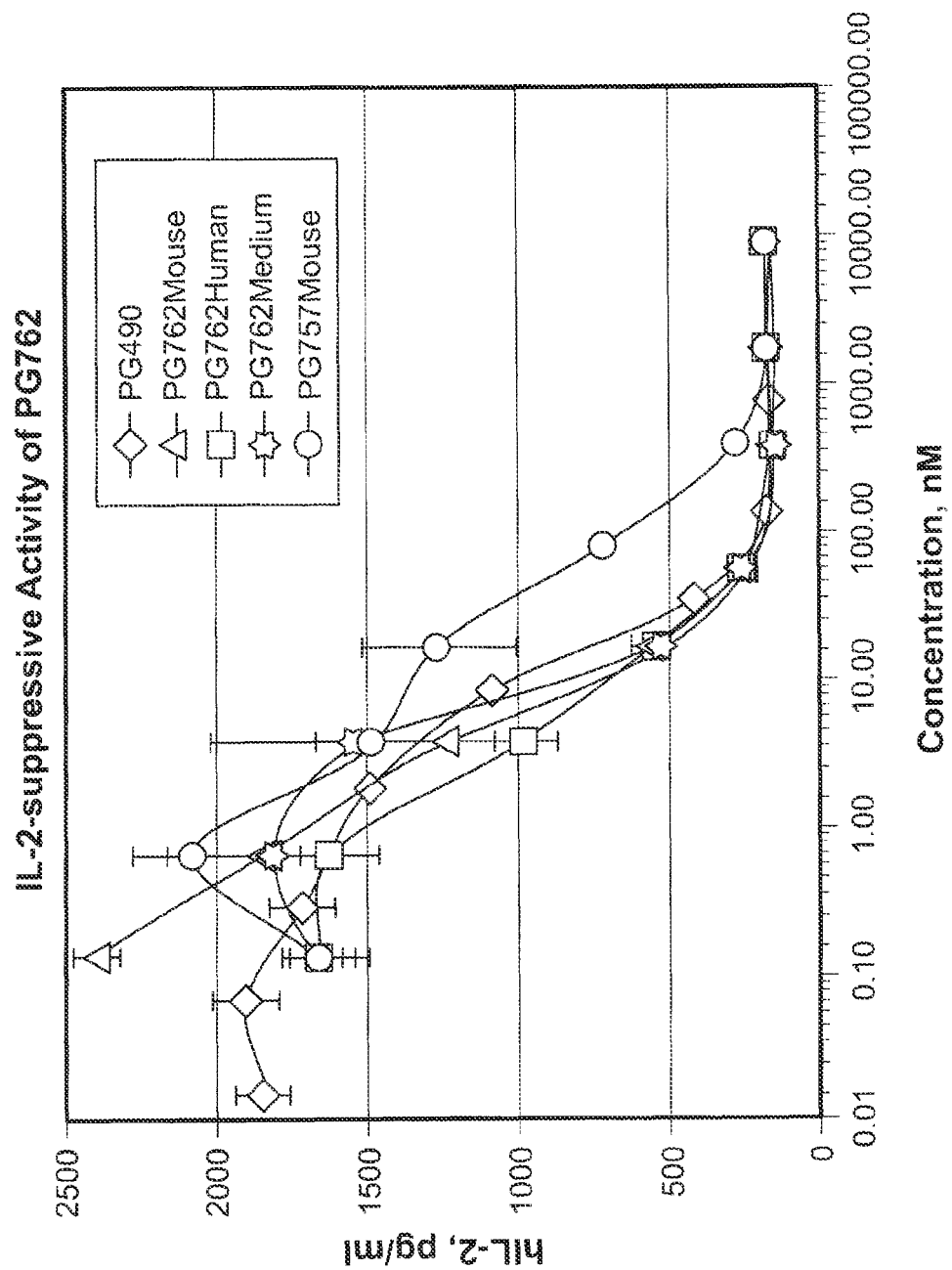
Figure 8:
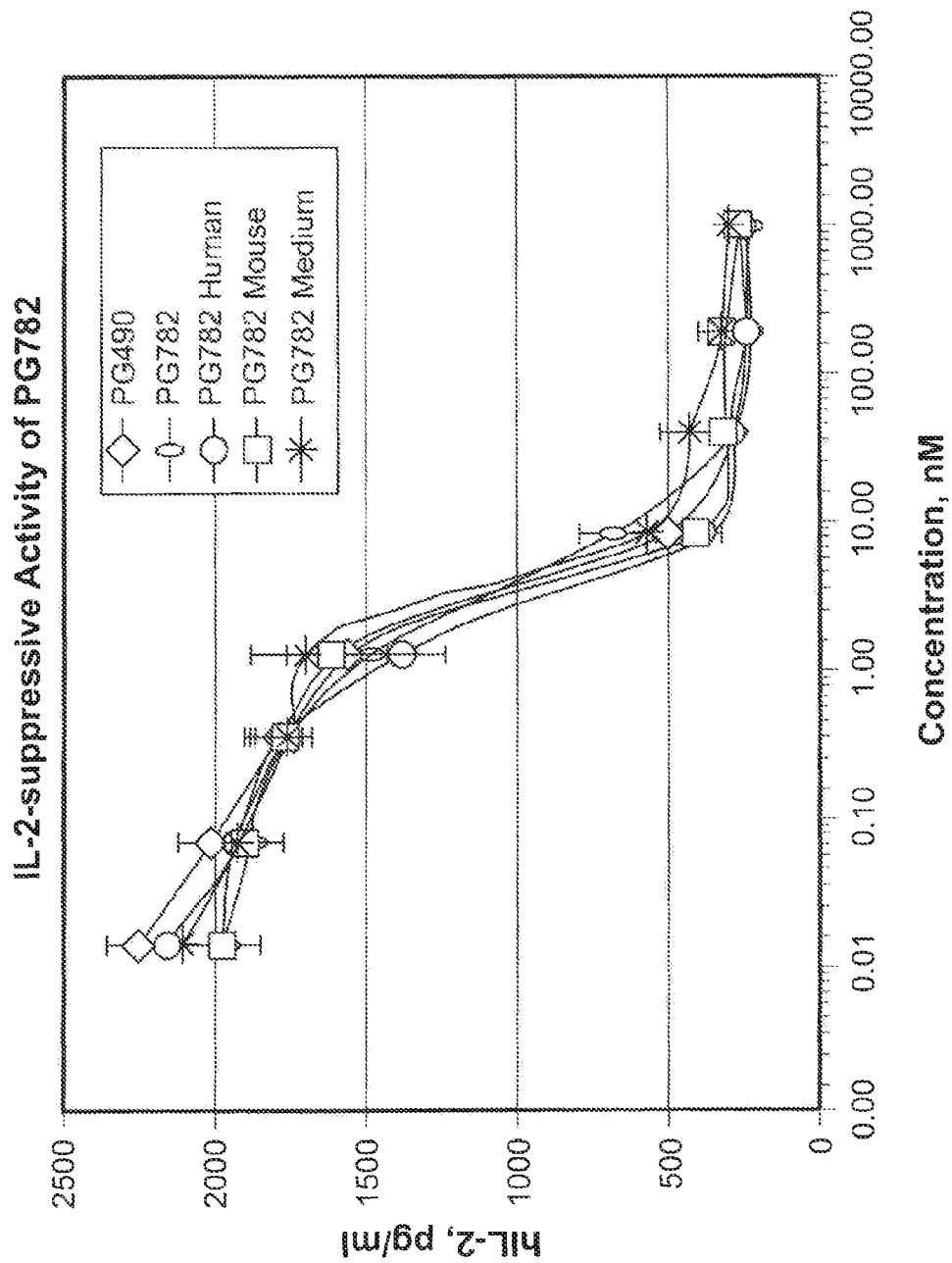

The results of the cytotoxic assays are shown in FIGS. 3-5, and the results of the IL-2 immunosuppression assays are shown in FIGS. 6-8. In the figure legends, "mouse", "human" and "monkey" refer to serum used for incubation. The designation "unconverted" or no designation indicates that the compound was not incubated in serum. Incubation in serum is expected to convert the compounds to triptolide, and this was shown to happen within about 5 minutes for PG757 and PG762.

As shown in FIG. 3, the compound PG757 incubated in serum was significantly more cytotoxic in the MIT assay than triptolide; see also Table 1 below. (The data for test compounds in the Table is for compounds incubated in serum for 24 hrs.) Incubated PG782 was also more potent than triptolide, and incubated PG762 was of comparable potency. As shown in FIGS. 6-8, all of the test compounds, when incubated in serum, were comparable to triptolide in suppression of IL-2.

TABLE 1

| Compound | Viability/Cytotoxicity MTT (ED$_{50}$) | immunosuppression IL-2 (IC$_{50}$) |
|---|---|---|
| PG490 (triptolide) | 60 nM | 4 nM |
| PG757 | 32 nM | 9 nM |
| PG762 | 60 nM | 9 nM |
| PG782 | 53 nM | 2 nM |

III. Therapeutic Compositions

Formulations containing the triptolide derivatives of the invention may take the form of solid, semi-solid, lyophilized powder, or liquid dosage forms, such as tablets, capsules, powders, sustained-release formulations, solutions, suspensions, emulsions, ointments, lotions, or aerosols, preferably in unit dosage forms suitable for simple administration of precise dosages. The compositions typically include a conventional pharmaceutical carrier or excipient and may additionally include other medicinal agents, carriers, or adjuvants. Preferably, the composition will be about 0.5% to 75% by weight of a compound or compounds of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

The composition may be administered to a subject orally, transdermally or parenterally, e.g., by intravenous, subcutaneous, intraperitoneal, or intramuscular injection. For use in oral liquid preparation, the composition may be prepared as a solution, suspension, emulsion, or syrup, being supplied either in liquid form or a dried form suitable for hydration in water or normal saline. For parenteral administration, an injectable composition for parenteral administration will typically contain the triptolide derivative in a suitable intravenous solution, such as sterile physiological salt solution.

Liquid compositions can be prepared by dissolving or dispersing the triptolide derivative (about 0.5% to about 20%) and optional pharmaceutical adjuvants in a pharmaceutically acceptable carrier, such as, for example, aqueous saline, aqueous dextrose, glycerol, or ethanol, to form a solution or suspension.

The compound may also be administered by inhalation, in the form of aerosol particles, either solid or liquid, preferably of respirable size. Such particles are sufficiently small to pass through the mouth and larynx upon inhalation and into the bronchi and alveoli of the lungs. In general, particles ranging from about 1 to 10 microns in size, and preferably less than about 5 microns in size, are respirable. Liquid compositions for inhalation comprise the active agent dispersed in an aqueous carrier, such as sterile pyrogen free saline solution or sterile pyrogen free water. If desired, the composition may be mixed with a propellant to assist in spraying the composition and forming an aerosol.

Methods for preparing such dosage forms are known or will be apparent to those skilled in the art; for example, see *Remington's Pharmaceutical Sciences* (19th Ed., Williams & Wilkins, 1995). The composition to be administered will contain a quantity of the selected compound in an effective amount for effecting immunosuppression in a subject or apoptosis in a targeted cell.

IV. Immunomodulating and Antiinflammatory Treatment

As shown in FIGS. 6-8, two compounds of formula I, designated PG757 and PG762, and a compound of formula II, designated PG782, inhibited IL-2 production in Jurkat cells (see Example 5) in a dose-dependent manner. The invention thus includes the use of the invention compounds as immunosuppressive agents, e.g. as an adjunct to transplant procedures or in treatment of autoimmune disease.

Immunoregulatory abnormalities have been shown to exist in a wide variety of autoimmune and chronic inflammatory diseases, including systemic lupus erythematosis, chronic rheumatoid arthritis, type I and II diabetes mellitus, inflammatory bowel disease, binary cirrhosis, uveitis, multiple sclerosis and other disorders such as Crohn's disease, ulcerative colitis, bullous pemphigoid, sarcoidosis, psoriasis, ichthyosis, Graves ophthalmopathy and asthma. Although the underlying pathogenesis of each of these conditions may be quite different, they have in common the appearance of a variety of autoantibodies and self-reactive lymphocytes. Such self-reactivity may be due, in part, to a loss of the homeostatic controls under which the normal immune system operates.

Similarly, following a bone-marrow transplant or other transplant of hematopoietic stem cells from a donor tissue source containing mature lymphocytes, the transferred lymphocytes recognize the host tissue antigens as foreign. These cells become activated and mount an attack upon the host (a graft-versus-host response) that can be life-threatening. Moreover, following an organ transplant, the host lymphocytes recognize the foreign tissue antigens of the organ graft and mount cellular and antibody-mediated immune responses (a host-versus-graft response) that lead to graft damage and rejection.

One result of an autoimmune or a rejection reaction is tissue destruction caused by inflammatory cells and the mediators they release. Anti-inflammatory agents such as NSAIDs act principally by blocking the effect or secretion of these mediators but do nothing to modify the immunologic basis of the disease. On the other hand, cytotoxic agents, such as cyclophosphamide, act in such a nonspecific fashion that both the normal and autoimmune responses are shut off. Indeed, patients treated with such nonspecific immunosuppressive agents are as likely to succumb from infection as they are from their autoimmune disease.

The compositions of the present invention are useful in applications for which triptolide and its prodrugs and other derivatives have proven effective, e.g. in immunosuppression therapy, as in treating an autoimmune disease, preventing transplantation rejection, or treating or preventing graft-versus-host disease (GVHD). See, for example, co-owned U.S. Pat. No. 6,150,539, which is incorporated herein by reference. Triptolide and the present derivatives are also useful for treatment of other inflammatory conditions, such as traumatic inflammation, and in reducing male fertility.

The compositions are useful for inhibiting rejection of a solid organ transplant, tissue graft, or cellular transplant from an incompatible human donor, thus prolonging survival and function of the transplant, and survival of the recipient. This use would include, but not be limited to, solid organ transplants (such as heart, kidney and liver), tissue grafts (such as skin, intestine, pancreas, gonad, bone, and cartilage), and cellular transplants (such as cells from pancreas, brain and nervous tissue, muscle, skin, bone, cartilage and liver).

The compositions are also useful for inhibiting xenograft (interspecies) rejection; i.e. in preventing the rejection of a solid organ transplant, tissue graft, or cellular transplant from a non-human animal, whether natural in constitution or bioengineered (genetically manipulated) to express human genes, RNA, proteins, peptides or other non-native, xenogeneic molecules, or bioengineered to lack expression of the animal's natural genes, RNA, proteins, peptides or other normally expressed molecules. The invention also includes the use of a composition as described above to prolong the survival of such a solid organ transplant, tissue graft, or cellular transplant from a non-human animal.

Also included are methods of treatment of autoimmune diseases or diseases having autoimmune manifestations, such as Addison's disease, autoimmune hemolytic anemia, autoimmune thyroiditis, Crohn's disease, diabetes (Type I), Graves' disease, Guillain-Barre syndrome, systemic lupus erythematosis (SIT), lupus nephritis, multiple sclerosis, myasthenia gravis, psoriasis, primary biliary cirrhosis, rheumatoid arthritis and uveitis, asthma, atherosclerosis, Hashimoto's thyroiditis, allergic encephalomyelitis, glomerulonephritis, and various allergies.

Further uses may include the treatment and prophylaxis of inflammatory and hyperproliferative skin diseases and cutaneous manifestations of immunologically mediated illnesses, such as psoriasis, atopic dermatitis, pemphigus, urticaria, cutaneous eosinophilias, acne, and alopecia areata; various eye diseases such as conjunctivitis, uveitis, keratitis, and sarcoidosis; inflammation of mucous and blood vessels such as gastric ulcers, vascular damage caused by ischemic diseases and thrombosis, ischemic bowel diseases, inflammatory bowel diseases, and necrotizing enterocolitis; intestinal inflammations/allergies such as Coeliac diseases and ulcerative colitis; renal diseases such as interstitial nephritis, Good-pasture's syndrome, hemolytic-uremic syndrome and diabetic nephropathy; hematopoietic diseases such as idiopathic thrombocytopenia purpura and autoimmune hemolytic anemia; skin diseases such as dermatomyositis and cutaneous T cell lymphoma; circulatory diseases such as arteriosclerosis and atherosclerosis; renal diseases such as ischemic acute renal insufficiency and chronic renal insufficiency; and Behcet's disease.

The compositions and method of the invention are also useful for the treatment of inflammatory conditions such as asthma, both intrinsic and extrinsic manifestations, for example, bronchial asthma, allergic asthma, intrinsic asthma, extrinsic asthma and dust asthma, particularly chronic or inveterate asthma (for example, late asthma and airway hyperresponsiveness). The composition and method may also be used for treatment of other inflammatory conditions, including traumatic inflammation, inflammation in Lyme disease, chronic bronchitis (chronic infective lung disease), chronic sinusitis, sepsis associated acute respiratory distress syndrome, and pulmonary sarcoidosis. For treatment of respiratory conditions such as asthma, the composition is preferably administered via inhalation, but any conventional route of administration may be useful.

In treating an autoimmune condition, the patient is given the composition on a periodic basis, e.g., 1-2 times per week, at a dosage level sufficient to reduce symptoms and improve patient comfort. For treating rheumatoid arthritis, in particular, the composition may be administered by intravenous injection or by direct injection into the affected joint. The patient may be treated at repeated intervals of at least 24 hours, over a several week period following the onset of symptoms of the disease in the patient. The dose that is administered is preferably in the range of 1-25 mg/kg patient body weight per day, with lower amounts being preferred for parenteral administration, and higher amounts being preferred for oral administration. Optimum dosages can be determined by routine experimentation according to methods known in the art.

For therapy in transplantation rejection, the method is intended particularly for the treatment of rejection of heart, kidney, liver, cellular, and bone marrow transplants, and may also be used in the treatment of GVHD. The treatment is typically initiated perioperatively, either soon before or soon after the surgical transplantation procedure, and is continued on a daily dosing regimen, for a period of at least several weeks, for treatment of acute transplantation rejection. During the treatment period, the patient may be tested periodically for immunosuppression level, e.g., by a mixed lymphocyte reaction involving allogeneic lymphocytes, or by taking a biopsy of the transplanted tissue.

In addition, the composition may be administered chronically to prevent graft rejection, or in treating acute episodes of late graft rejection. As above, the dose administered is preferably 1-25 mg/kg patient body weight per day, with lower amounts being preferred for parenteral administration, and higher amounts for oral administration. The dose may be increased or decreased appropriately, depending on the response of the patient, and over the period of treatment, the ability of the patient to resist infection.

In treatment or prevention of graft-versus-host disease, resulting from transplantation into a recipient of matched or mismatched bone marrow, spleen cells, fetal tissue, cord blood, or mobilized or otherwise harvested stem cells, the dose is preferably in the range 0.25-2 mg/kg body weight/day, preferably 0.5-1 mg/kg/day, given orally or parenterally.

Also within the scope of the invention is a combination therapy comprising a compound of formula I and one or more conventional immunosuppressive agents. These immunosuppressant agents within the scope of this invention include, but are not limited to, Imurek® (azathioprine sodium), brequinar sodium, Spanidin™ (gusperimus trihydrochloride, also known as deoxyspergualin), mizoribine (also known as bredinin), Cellcept® (mycophenolate mofetil), Neoral® (Cyclosporin A; also marketed as a different formulation under the trademark Sandimmune®), Prograf™ (tacrolimus, also known as FK-506), Rapimmune® (sirolimus, also known as rapamycin), leflunomide (also known as HWA-486), Zenapax®, glucocorticoids, such as prednisolone and its derivatives, antibodies such as orthoclone (OKT3), and antithymyocyte globulins, such as thymoglobuiins. The compounds are useful as potentiators when administered concurrently with another immunosuppressive drug for immunosuppressive treatments as discussed above. A conventional immunosuppressant drug, such as those above, may thus be administered in an amount substantially less (e.g. 20% to 50% of the standard dose) than when the compound is administered alone. Alternatively, the invention compound and immunosuppressive drug are administered in amounts such that the resultant immunosuppression is greater than what would be expected or obtained from the sum of the effects obtained with the drug and invention compound used alone. Typically, the immunosuppressive drug and potentiator are administered at regular intervals over a time period of at least 2 weeks.

The compositions of the invention may also be administered in combination with a conventional anti-inflammatory drug (or drugs), where the drug or amount of drug administered is, by itself, ineffective to induce the appropriate suppression or inhibition of inflammation.

Immunosuppressive activity of compounds in vivo can be evaluated by the use of established animal models known in the art. Such assays may be used to evaluate the relative effectiveness of immunosuppressive compounds and to estimate appropriate dosages for immunosuppressive treatment. These assays include, for example, a well-characterized rat model system for allografts, described by Ono and Lindsey (1969), in which a transplanted heart is attached to the abdominal great vessels of an allogeneic recipient animal, and the viability of the transplanted heart is gauged by the heart's ability to beat in the recipient animal. A xenograft model, in which the recipient animals are of a different species, is described by Wang (1991) and Murase (1993). A model for evaluating effectiveness against GVHD involves injection of normal F1 mice with parental spleen cells; the mice develop a GVHD syndrome characterized by splenomegaly and immunosuppression (Korngold, 978; Gleichmann, 1984). Single cell suspensions are prepared from individual spleens, and microwell cultures are established in the presence and absence of concanavalin A to assess the extent of mitogenic responsiveness.

V. Anticancer Treatment

As shown in FIGS. 3-5, two compounds of formula I, designated PG757 and PG762, and a compound of formula II, designated PG782, were cytotoxic to Jurkat cells (see Example 4) in a dose-dependent manner. The invention thus includes the use of the invention compounds as cytotoxic agents, particularly to treat cancers. As used herein, "cancer" refers to all types of cancer or neoplasm or malignant tumors found in mammals especially humans, including leukemias, sarcomas, carcinomas and melanoma.

The term "leukemia" refers broadly to progressive, malignant diseases of the blood-forming organs and is generally characterized by a distorted proliferation and development of leukocytes and their precursors in the blood and bone marrow. The term "sarcoma" generally refers to a tumor which is made up of a substance like the embryonic connective tissue and is generally composed of closely packed cells embedded in a fibrillar or homogeneous substance. The term "melanoma" is taken to mean a tumor arising from the melanocytic system of the skin and other organs. The term "carcinoma" refers to a malignant new growth made up of epithelial cells tending to infiltrate the surrounding tissues and give rise to metastases.

Included, for example, are cancers involving cells derived from reproductive tissue (such as Sertoli cells, germ cells, developing or more mature spermatogonia, spermatids or spermatocytes and nurse cells, germ cells and other cells of the ovary), the lymphoid or immune systems (such as Hodgkin's disease and non-Hodgkin's lymphomas), the hematopoietic system, and epithelium (such as skin, including malignant melanoma, and gastrointestinal tract), solid organs, the nervous system, e.g. glioma (see Y. X. Zhou et al., 2002), and musculo-skeletal tissue. The compounds may be used for treatment of various cancer cell types, including, but not limited to, brain, including medulloblastoma, head and neck, breast, colon, small cell lung, large cell lung, thyroid, testicle, bladder, prostate, liver, kidney, pancreatic, esophogeal, stomach, ovarian, cervical or lymphoma tumors. Treatment of breast, colon, lung, and prostate tumors is particularly contemplated.

The compositions may be administered to a patient afflicted with cancer and/or leukemia by any conventional route of administration, as discussed above. The method is useful to slow the growth of tumors, prevent tumor growth, induce partial regression of tumors, and induce complete regression of tumors, to the point of complete disappearance. The method is also useful in preventing the outgrowth of metastases derived from solid tumors.

The compositions of the invention may be administered as sole therapy or with other supportive or therapeutic treatments not designed to have anti-cancer effects in the subject. The method also includes administering the invention compositions in combination with one or more conventional anti-cancer drugs or biologic protein agents, where the amount of drug(s) or agent(s) is, by itself, ineffective to induce the appropriate suppression of cancer growth, in an amount effective to have the desired anti-cancer effects in the subject. Such anti-cancer drugs include actinomycin D, camptothecin, carboplatin, cisplatin, cyclophosphamide, cytosine arabinoside, daunorubicin, doxorubicin, etoposide, fludarabine, 5-fluorouracil, hydroxyurea, gemcitabine, irinotecan, methotrexate, mitomycin C, mitoxantrone, paclitaxel, taxotere, teniposide, topotecan, vinblastine, vincristine, vindesine, and vinorelbine. Anti-cancer biologic protein agents include tumor necrosis factor (TNF), TNF-related apoptosis inducing ligand (TRAIL), other TNF-related or TRAIL-related ligands and factors, interferon, interleukin-2, other interleukins, other cytokines, chemokines, and factors, antibodies to tumor-related molecules or receptors (such as anti-HER2 antibody), and agents that react with or bind to these agents (such as members of the TNF super family of receptors, other receptors, receptor antagonists, and antibodies with specificity for these agents).

Antitumor activity in vivo of a particular composition can be evaluated by the use of established animal models, as described, for example, in Fidler et al., U.S. Pat. No. 6,620,843. Clinical doses and regimens are determined in accordance with methods known to clinicians, based on factors such as severity of disease and overall condition of the patient.

VI. Other Indications

The compounds of the present invention may also be used in the treatment of certain CNS diseases. Glutamate fulfills numerous physiological functions, including an important role in the pathophysiology of various neurological and psychiatric diseases. Glutamate excitotoxicity and neurotoxicity have been implicated in hypoxia, ischemia and trauma, as well as in chronic neurodegenerative or neurometabolic diseases, Alzheimer's dementia, Huntington's disease and Parkinson's disease. In view of the reported neuroprotective effects of triptolide, particularly protection from glutamate-induced cell death (Q. He et al., 2003; X. Wang et al., 2003), compounds of the invention are envisioned to antagonize the neurotoxic action of glutamates and thus may provide a useful therapy for such diseases.

Recent evidence from MS patients in relapse suggests an altered glutamate homeostasis in the brain. Neurotoxic events occurring in MS patients can be responsible for oligodendrocyte and neuronal cell death. Antagonizing glutamate receptor-mediated excitotoxicity by treatment with compounds of this invention may have therapeutic implications in MS patients. Other CNS and neurodegenerative diseases such as Guillain-Barre syndrome, Meniere's disease, polyneuritis, multiple neuritis, mononeuritis radiculopathy, Alexander's disease, Alper's disease, amyotrophic lateral sclerosis, Ataxia telangiectasia, Batten disease, bovine spongiform encephalopathy (BSE), Canavan's disease, Cockayne's syndrome, corticobasal degeneration, Creutzfeldt-Jakob's disease, Huntington's disease, HIV-associated dementia, Kennedy's disease, Krabbe's disease, Lewy body dementia, Machado-Joseph's disease (Spinocerebellar ataxia type 3), multiple system atrophy, Pelizaeus-Merzbacher's Disease, Pick's disease, primary lateral sclerosis, Refsum's disease, Sandhoff's disease, Schilder's disease, schizophrenia, spinocerebellar ataxia, spinal muscular atrophy, Steele-Richardson-Olszewski's disease, and Tabes dorsalis, may also be treated with the compounds of the present invention.

The compounds of the present invention may also be used in the treatment of organ fibrosis (e.g., lung and liver). Idiopathic pulmonary fibrosis (PP) is a progressive interstitial lung disease with no known etiology. PF is characterized by excessive deposition of intracellular matrix and collagen in the lung interstitium and gradual replacement of the alveoli by scar tissue as a result of inflammation and fibrosis. As the disease progresses, the increase in scar tissue interferes with the ability to transfer oxygen from the lungs to the bloodstream. A 14-succinimide ester of triptolide has been reported to block bleomycin-induced PP (G. Krishna et al., 2001). Accordingly, the compounds of the present invention may be useful for treatment of PF. Treatment of other respiratory diseases, such as sarcoidosis, fibroid lung, and idiopathic interstitial pneumonia is also considered.

Other diseases involving the lung and envisioned to be treatable by compounds of this invention include Severe Acute Respiratory Syndrome (SARS) and acute respiratory distress syndrome (ARDS). In particular, with respect to SARS, the reduction of virus content (SARS-CoV) before the peak of the disease process and the usefulness of corticosteroid treatment, as noted below, suggest that the development of the most severe, life-threatening effects of SARS may result from the exaggerated response of the body to the infection (immune hyperactivity) rather than effects of the virus itself (See also co-owned PCT Publication No. WO 2005/020887, which is incorporated herein by reference.) Corticosteroid treatment has been used in SARS patients to suppress the massive release of cytokines that may characterize the immune hyperactive phase, in the hope that it will stop the progression of pulmonary disease in the next phase. Corticosteroid treatment has produced good clinical results in reduction of some of the major symptoms of SARS. However, there are several treatment-related side effects, and there is a clear need for more selective immunosuppressive and/or anti-inflammatory agents.

EXAMPLES

The following examples are intended to illustrate but not in any way limit the invention.

Example 1

Preparation of PG757 and PG762

A mixture of triptolide (PG490) (360 mg, 1.0 mmol) and Et$_3$N (103 mg, 1.02 mmol) CH$_2$Cl$_2$, (5 mL) was added dropwise to a solution of phosgene (101 mg, 1.02 mmol) in dry CH$_2$Cl$_2$ (25 mL) cooled to −78° C. (dry ice and acetone). Then the temperature of the reaction mixture was slowly increased to −20° C. The precipitate of Et$_3$NHCl that formed was filtered off, and the solvent was removed under reduced pressure. The product was purified by column chromatography using silica gel. The major product obtained was the diepoxide PG762, shown below and in FIG. 18. The ring-opened analog, PG757, was obtained as a side product. It can be converted to PG762 using a base such as DBU (1,8-diazabicyclo[5.4.0]undec-7-ene).

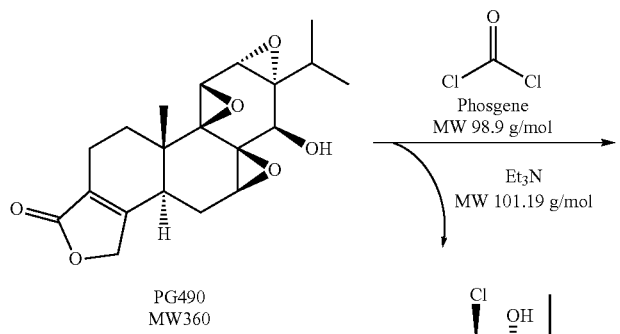
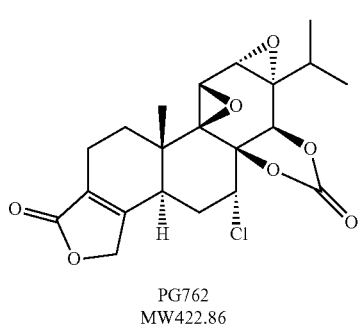

Example 2

Preparation of PG830

Figure 1C:
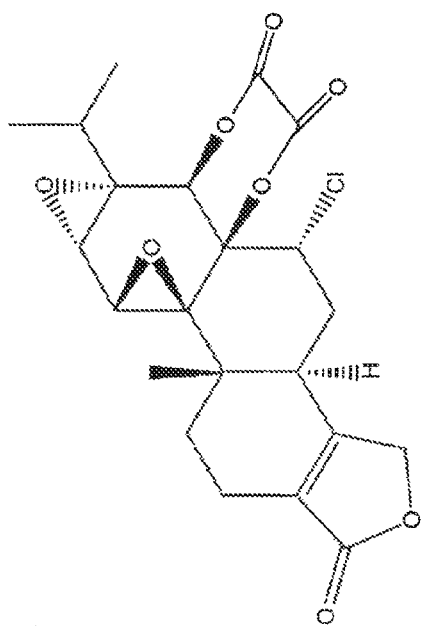
Figure 1A:
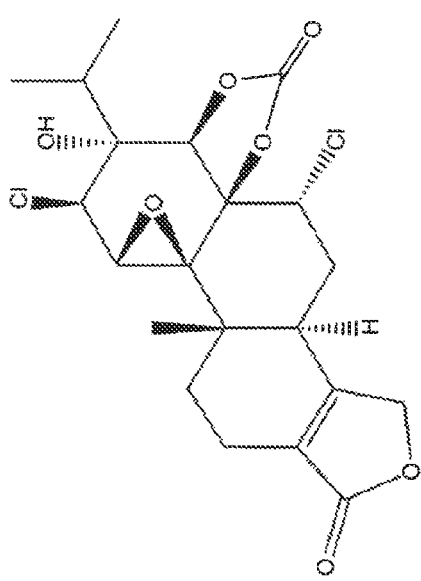

A mixture of triptolide (PG490) (360 mg, 1.0 mmol) and Et₃N (103 mg, 1.02 mmol) in benzene (8 ml) was added dropwise to a solution of oxalyl chloride (130 mg, 1.02 mmol) in dry benzene (10 mL) cooled in an ice bath under an inert atmosphere. The temperature of the reaction mixture was then allowed to reach room temperature, and the precipitate of Et₃NHCl that formed was filtered off under an inert atmosphere. The filtrate was gently heated for 1.5 h, and solvent was evaporated in vacuo. The resulting solid was purified on silica gel to give PG830, shown below and in FIG. 1C.

Example 3

Preparation of PG782

Figure 2:
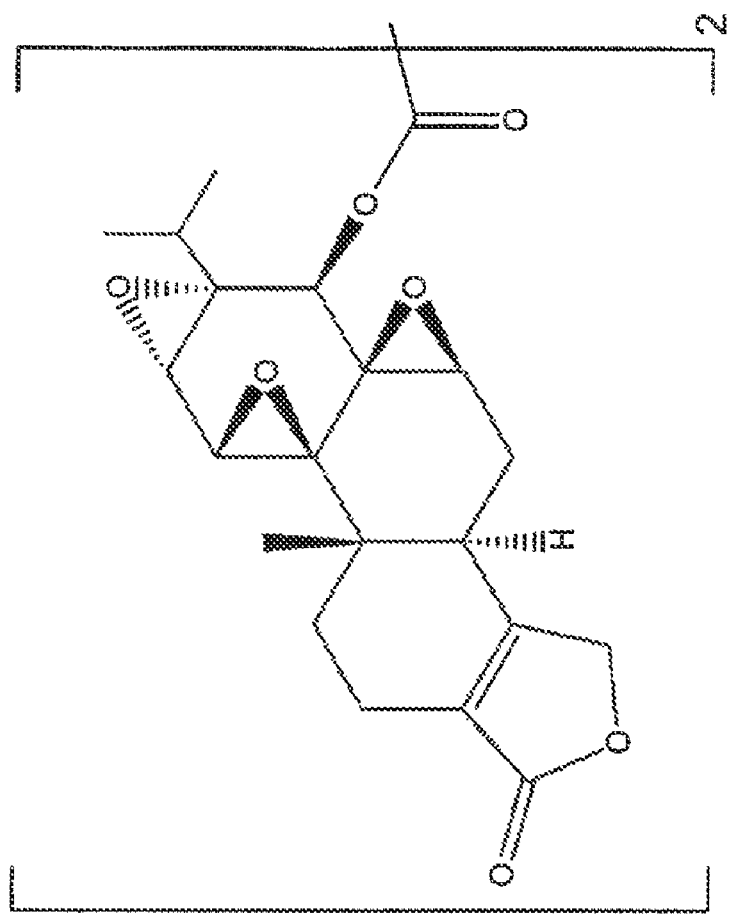
FIG. 2 shows an exemplary compound of the invention which is an embodiment of structure II herein.

A solution of oxalyl chloride (130 mg, 1.02 mmol) CH₂Cl₂ (5 mL) was added dropwise to a solution of triptolide (PG490) (720 mg, 2.0 mmol) and Et₃N (103 mg, 1.02 mmol) in dry CH₂Cl₂ (10 mL) cooled to −45° C. The temperature of the reaction mixture was increased to −20° C., and the precipitate of Et₃NHCl that formed was filtered off. The solvent was evaporated in vacuo, and the solid residue was purified by column chromatography on silica gel to give PG782, shown below and in FIG. 2.

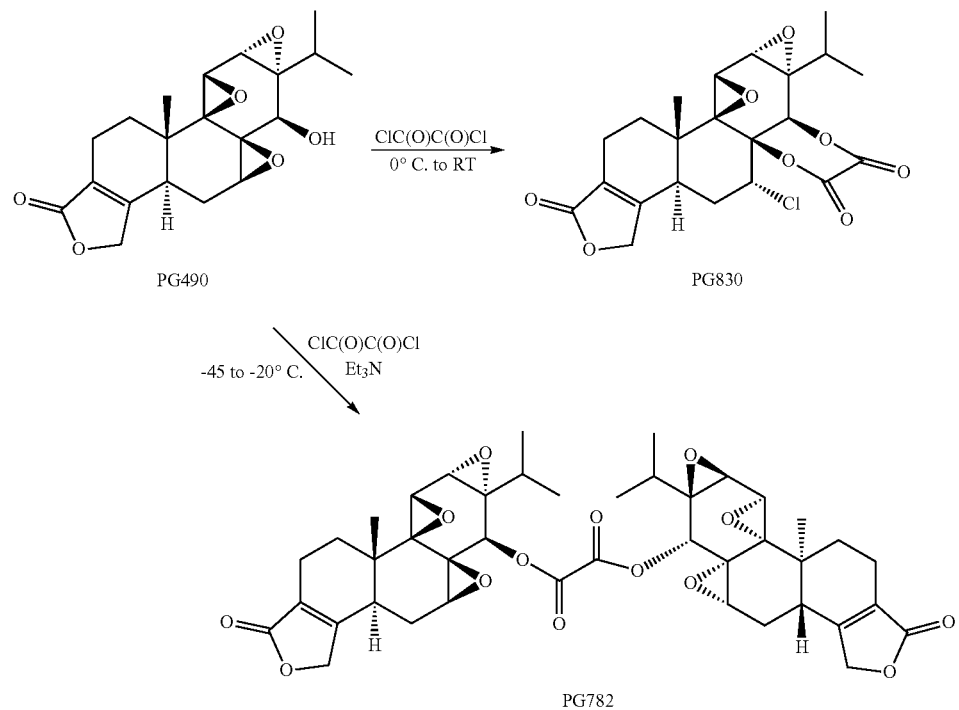

Example 4

Cytotoxicity (MTT) Assay

Test compounds were incubated in serum or medium for 24 h at 37° C. Human T cell lymphoma (Jurkat) cells were cultured in the presence of indicated concentrations of the test compound or triptolide (PG490) for 24 h in 100 ml/well RPMI1640 complete medium.

Cytotoxicity of the compounds was determined in a standard MTT assay using Cell Proliferation Kit I (#1 465 007, Roche Diagnostics, Mannheim, Germany). In a typical assay, Jurkat cells ($4\times10^5$ per well) were cultured for 24 h, in 96-well tissue culture plates, in the presence of serial three-fold dilutions of test compounds or medium. The cultures were then supplemented with 10 µl/well MTT reagent for 4 h and then with 0.1 ml/well solubilizing reagent for an additional 16 h. Optical density at 570 nm ($OD_{570}$) was measured on a ThermoScan microplate reader (Molecular Devices, Menlo Park, Calif.).

The data is presented as $OD_{570}$ values versus concentration of the compounds. The results for invention compounds PG757, PG762, and PG782, compared with triptolide (PG490) and a medium control, are given in FIGS. 3-5, respectively.

Example 5

IL-2 Production Assay

Jurkat cells ($10^7$/ml) were stimulated with 50 ng/ml PMA and 10 mg/ml PHA in the presence of indicated concentrations of triptolide (PG490) or test compound, incubating for 24 hrs. The plates were centrifuged to pellet the cells, 150 µl of supernatant was removed from each well, and the samples were stored at −20° C. The stored supernatants were analyzed for human IL-2 concentration using the Luminex 100 (Luminex Corporation, Austin, Tex.), Luminex microspheres coupled with anti-IL-2 capture antibody, and fluorochrome-coupled anti-IL-2 detection antibody.

The data were expressed as pg/ml of IL-2 and plotted as the concentration of compound versus IL-2 concentration. The results for invention compounds PG757, PG762, and PG782, compared with triptolide (PG490) and a medium control, are given in FIGS. 6-8, respectively.

It is claimed:

1. A compound having the structure I:

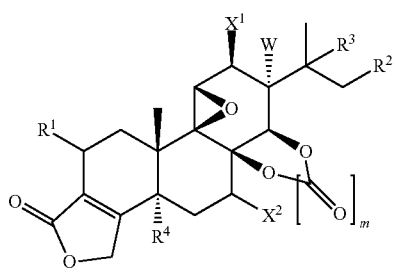

where each of $R^1$, $R^2$, $R^3$, and $R^4$ is independently selected from hydrogen, hydroxy —O(CO)$_n$X, —O(CO)$_n$OR$^5$, and —O(CO)$_n$N(R$^5$)$_2$, where X is halogen, $R^5$ is hydrogen or lower alkyl, and n is 1-2, with the proviso that at least three of $R^1$, $R^2$, $R^3$, and $R^4$ are hydrogen;

m is 1-2;

$X^2$ is halogen; and $X^1$ is halogen and W is hydroxyl, or $X^1$ and W together form an epoxy group.

2. The compound of claim 1, wherein each of $R^1$, $R^2$, $R^3$, and $R^4$ is hydrogen.

3. The compound of claim 1, wherein halogen is F or Cl.

4. The compound of claim 1, wherein n=1.

5. The compound of claim 1, wherein $X^1$ is halogen and W is hydroxyl.

6. The compound of claim 5, wherein $X^1$ is Cl.

7. The compound of claim 1, wherein m=1.

8. A compound having the structure II:

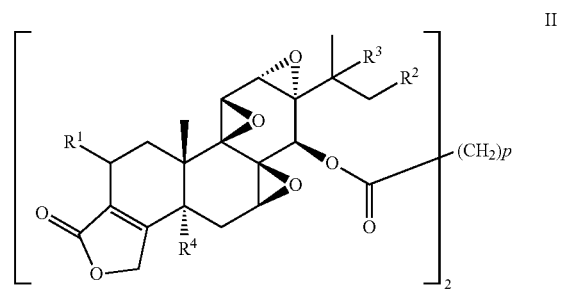

where each, $R^1$, $R^2$, $R^3$, and $R^4$ is independently selected from hydrogen, hydroxyl, —O(CO)$_n$X, —O(CO)$_n$OR$^5$, and —O(CO)$_n$N(R$^5$)$_2$, where X is halogen, $R^5$ is hydrogen or lower alkyl, and n is 1-2, with the proviso that at least three of $R^1$, $R^2$, $R^3$, and $R^4$ are hydrogen; and p is 0-4.

9. The compound of claim 8, wherein n=1.

10. The compound of claim 8, wherein halogen is Cl.

11. The compound of claim 8, wherein each of $R^1$, $R^2$, $R^3$, and $R^4$ is hydrogen.

12. The compound of claim 8, wherein p=0.

13. A method of inhibiting production of IL-2 in cells comprising administering to a subject in need of such treatment, in a pharmaceutically acceptable vehicle, an effective amount of a compound of claim 1 or claim 8.

14. A method of inducing apoptosis in a cell, comprising contacting said cell with an effective amount of a compound of claim 1 or claim 8.

* * * * *